United States Patent [19]

Trabucco

[11] 4,136,702

[45] Jan. 30, 1979

[54] CATHETER-TYPE ELECTRODE MEMBER FOR AN IMPLANTABLE PACEMAKER

[76] Inventor: Hector O. Trabucco, 2926 Av. Santa Fe, Buenos Aires, Argentina

[21] Appl. No.: 875,849

[22] Filed: Feb. 7, 1978

[30] Foreign Application Priority Data

Feb. 14, 1977 [AR] Argentina ............................ 266538

[51] Int. Cl.² ............................................. A61N 1/04
[52] U.S. Cl. ................................. 128/418; 128/419 P
[58] Field of Search ............................. 128/418, 419 P

[56] References Cited

U.S. PATENT DOCUMENTS

| 3,976,082 | 8/1976 | Schmitt | 128/418 |
| 3,978,865 | 9/1976 | Trabucco | 128/418 |
| 4,066,085 | 1/1978 | Hess | 128/418 |

*Primary Examiner*—William E. Kamm
*Attorney, Agent, or Firm*—Ladas, Parry, Von Gehr, Goldsmith & Deschamps

[57] ABSTRACT

A catheter type electrode member for an implantable pacemaker, insertable from without from the epicardium into the heart muscle for cardiac stimulation, of the type comprising a holder of dielectric elastic material including a stem terminating in an enlarged resilient pad having the shape of a platform. One major surface of the platform pivotally supporting an arcuately curved electricity conducting hook, which projects out of said pad and has its tip portion pointing back towards said major surface and preferably two spaced apart anchoring needles likewise projecting out from said major surface, conveniently in a diverging manner. Upon insertion from the outside through the epicardium of the hook into the heart muscle by a tool gripping the hook, release of the hook allows the elastic pad to expand against the outer heart surface at the same time as the anchoring needles are made to penetrate also into the epicardium, thereby positively anchoring the electrode member in position. The hook is pivotally connected to a conductor passing through said pad and stem, and to be connected to an electric pulse generator.

1 Claim, 10 Drawing Figures

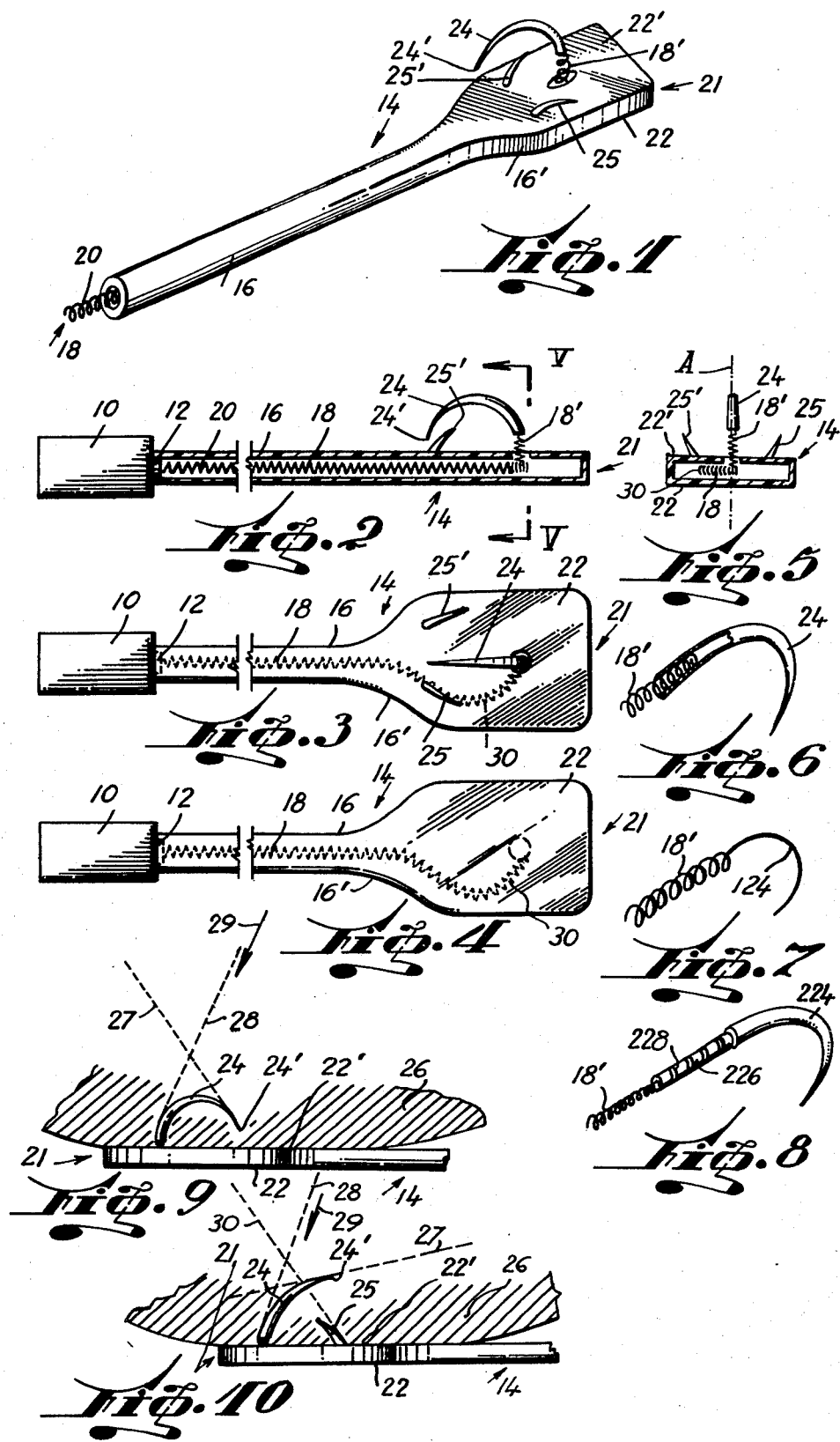

CATHETER-TYPE ELECTRODE MEMBER FOR AN IMPLANTABLE PACEMAKER

BACKGROUND OF THE INVENTION

1. Field of the Invention

This invention relates to an improvement for a catheter-type electrode member for an implantable pacemaker, insertable from without through the epicardium into the heart muscle for cardiac stimulation, with regard to the electrode member disclosed in my U.S. Pat. No. 3,978,865, granted on Sept. 7, 1976. Similarly as in my earlier patent, the improved electrode member of the present invention is to form part of an implantable pacemaker, for conveying electric stimuli to the epicardiac and eventually to the intramyocardiac zone of the heart, upon energization by an electric pulse generator.

2. Description of the Prior Art

A comment about the conventional catheter-type electrode members has already been made in my above cited patent, so that repetition becomes unnecessary, it being sufficient to point out that in those known conventional electrode members it was necessary to suture the platform to the heart muscle, after insertion of the conductor into at least the epicardium, to prevent any dislodgment of the tip of the conductor by the beating movement of the heart muscle.

The catheter-type electrode member of the aforementioned U.S. Patent provides for the insertion of the conductor into the epicardium without requiring any additional surgical intervention to suture the platform to the heart muscle. While this catheter type electrode member operates satisfactorily when inserted by a skilled surgeon, practice has shown that when the electrode is used by a surgeon who has not yet carried out a sufficient number of operations in this particular field and bearing in mind that the surgeon has to implant the hook shaped member which is the electricity conducting member in the patient's heart muscle while the heart is beating, it may be that the forward movement of the hook shaped electricity conducting member becomes barred due to special pathological circumstances of the heart. Thus, the tip of the hook will not be facing the major surface of the platform upon concluding the insertion into for instance the epicardium thereby tending to straighten the hook. In this event the continuous beating movement of the heart may eject the hook from the heart. To avoid this, as a safety measure, the platform according to the present invention, is provided with at least one generally straight shaped needle-like anchoring means projecting from the same flat major surface of the platform from which also the hook projects and said needle-like anchoring means projects at such an angle that its axis crosses at an acute angle the tangent line passing the generally semicircular shaped hook at the point of connection of the latter with the conductor, which is usually a helically coiled portion, which sligthly projects out of said flat major surface of the platform. Because of such crossing arrangement of the two parts hereinabove described, a positive lock is forwarded, so that the tendency ejecting the imperfectly located hook becomes barred, as soon as the platform, due to its resiliency will become in abutting relationship with the outside face of the heart muscle and thereby also inserting the anchoring means into the epicardium, as will be better understood later on.

In some prior art devices the electrode comprises a platform which instead of being sutured with suture string, has at the edges of the platform a plurality of spaced apart hook-shaped anchoring needles. These hook-shaped anchoring needles do not operate in combination, as far as the anchoring is concerned with the actual electrode member, which is always a straight member, so that there is no interaction, as in my proposed invention, of the anchoring means with the actual conductor of electricity. In other words these known hook-shaped needles are hooked into the heart, once the electrode has been inserted. These needles have to provide sufficient force to retain the platform against the outside face of the heart muscle, to assure that the straight conductor will not move within the perforated portion of the epicardium. In practice it can not be avoided that in those arrangements, which are not of the safest type, the tissues of the heart muscle become damaged due to an unavoidable amount of movement of the actual electricity conducing conductor inserted with it straight end portion in the epicardium. In addition, it is extremely difficult to properly locate these known types of electrodes, because while the heart muscle is beating, the latter has to be perforated to insert the straight electrode tip and then it has to be maintained by hand in the inserted position, while each of the hooks at the edge portions of the pad has to be anchored by separate steps.

SUMMARY OF THE INVENTION

A catheter-type electrode member for an implantable pacemaker, insertable from without through the epicardium into the heart muscle for cardiac stimulation, in accordance with the present invention, comprises a holder of dielectric material including a stem and an enlarged elastic pad having a substantially flat major surface; conductor means connectable to an external source of electric pulses, said conductor means extending through said stem into said pad and forming therein a helically coiled portion projecting outwardly from the said major surface; said helically coiled portion terminating beyond said major surface in an arcuately curved electricity conducting hook of generally semicircular shape, rising from the outwardly projecting helically coiled portion and being located above said major surface of said pad and having a tip pointing back towards said major surface for holding said pad in a suturless manner onto the heart surface upon penetrating the epicardium, with exertion of resilient pressure by said pad upon the heart; and at least one generally straight shaped needle-like anchoring means projecting from said substantially flat major surface at such an angle that its axis crosses at an acute angle the tangent line passing said generally semicircular shaped hook at the point of connection with said outwardly projection helically coiled portion.

In a preferred embodiment two spaced apart needles are used as anchoring means, and these may eventually be arranged in a diverging manner from the previously named flat major surface.

For the purpose of the present specification and appendant claims, the expression "to cross" which appears in relationship with the axis of the needle-like anchoring means in combination with the cited tangent line of the generally semi-circular shaped hook, is to be interpreted as covering the possibility where the anchoring means is located in a vertical plane which is generally parallel to the plane in which the hook is located or that both the needle-like anchoring means and the semi-circular shaped hook are arranged in the same vertical plane. In the latter event the axis will actually intersect the tangent line, while in the first event the axis of each needle-like anchoring means actually crosses, but does not intersect said tangent line. Therefore, the word "cross" is to be interpreted as being a common denominator for the two possibilities.

In use, the surgeon implants the hook through the epicardium in the patient's heart muscle as described in my previous patent and thereafter by exerting pressure on the outside of the platform inserts also the needle-like anchoring means.

BRIEF DESCRIPTION OF THE DRAWINGS

The above and other features of my invention will now be described in detail, with reference to the accompanying drawings, in which:

FIG. 1 is a perspective view of an electrode member according to the improvement of the present invention.

FIG. 2 is a longitudinal sectional view of the electrode member of FIG. 1;

FIG. 3 is a top plan view of the electrode member shown in FIGS. 1 and 2;

FIG. 4 is a bottom plan view of the same electrode member;

FIG. 5 is a cross-sectional view taken on the line V—V of FIG. 2;

FIG. 6 is a detail in perspective view;

FIGS. 7 and 8 are similar to FIG. 6, and show two alternative embodiments.

FIG. 9 schematically shows the correct location of the catheter type electrode in the heart muscle, when located by a skilled surgeon and where actually the anchoring means would become unnecessary.

FIG. 10 is a schematic illustration similar to the one of FIG. 9, but showing the case in which the additional anchoring means have to act, to avoid the ejection of the electricity conducting, arcuately curved hook of the conductor means.

SPECIFIC DESCRIPTION

As may be seen in FIGS. 1 to 4 an electrode member 14, in accordance with the present invention, is provided for an implantable pacemaker and which to this end is to be connected to an electric pulse generator 10, schematically shown in FIGS. 2 to 4, of a construction well known per se.

The electrode member 14 comprises a resilient, preferably transparent tubular stem 16 of dielectric material e.g. a synthetic elastomer, which surrounds a flexible electrical conductor 18 the left-hand end 20 (as seen in FIGS. 1 and 2), of which engages a supply terminal 12 at the output of the generator 10. The conductor 18 is a helically wound wire, having a high degree of flexiblity. The stem 16 integrally terminates at its forward, right-hand end 16' (as seen in FIGS. 3 and 4) in a flat, resilient, preferably also transparent pad 21 in the shape of a platform with two parallel major surfaces 22, 22', the spacing of which preferably equals the outer diameter of the electrical conductor 18 and the left-hand end portion of which platform or pad 21 merges into the stem 16. The pad 21 may either be hollow or filled with a suitable filler (not shown). The right-hand extremity 18' (see FIGS. 3 and 5) is a helically wound conductor portion which projects perpendicularly outwardly along an axis A, through the major surface 22' of the otherwise imperforated pad 21. The portion of the wire coil 18 which is received within the pad 21 follows preferably a soft curve 30. As shown in FIGS. 1 to 6, extremity 18' projecting from the major surface 22' is rigid with a sharp-pointed hook 24 swivelable about axis A; hook 24 extends along a nearly semi-circular arc in a plane including this axis A, its pointed end being biased preferably rearwardly so as to normally face the pad 21 and more particularly the major surface 22'.

As best seen in FIG. 6, the hook 24 has a hollow shank into which the wire extremity 18' is press-fitted.

According to an alternative embodiment shown in FIG. 7, the conductor extremity 18' is integrally extended to form hook 124 of the shape described above.

In FIG. 8 a further alternative structure of a hook 224 is shown, having a reduced shank 226, provided with a helical groove 228, into which the coil extremity 18' is threaded, so as to embrace that shank without increasing its effective thickness.

In all the embodiments the pointed end of the hook 24, 124, 224, is preferably solid.

The pad 22 is of a resilient type and has in the improved embodiment according to the present invention, additional anchoring means consisting of two generally straight needles 25, 25' which are arranged in a zone which faces the tip 24' of the hook 24; each needle defines an acute angle with the major surface 22' of the pad 21. The respective tips of said needles 24, 24' are directed towards the zone where the hook 24 is linked to the extremity 18' of the wire or helical conductor 18.

Referring now to FIG. 9, a portion of a patient's heart 26 is shown, into which the hook 24 has been correctly inserted, so that its tip 24' faces the major surface 22' of the pad 21. When the catheter-type electrode member 14 is inserted into the patient's thorax-cavity the hook 24 is hooked in proper place within the epicardium of the heart 26, such hook 24 will properly act as an anchoring means and will not become ejected by the beating heart, since the tip 24' adopts such a position that the tangent line 27 which passes through said tip 24' bisects at an acute angle (anchoring angle) the tangent line 28 which passes through the rear end portion of the hook 24 and more particularly where the latter is connected to the extremity 18' of the helically wound conductor 18. In this event, no additional anchoring means 25, 25' are necessary and they are not even shown in FIG. 9, since the movement of the heart muscle 26 which will exert a force approximately in the direction indicated by arrow 29 cannot remove the hook 24, because its tip 24' and more particularly the tangent line 27 crosses the direction of arrow 29 which is approximately equivalent to the tangent line 28 at an acute angle, which is an anchoring angle. This catheter-type electrode remains permanently anchored in the heart muscle 26, no matter at which inclination the hook 24 has been inserted in the heart 26, with regard to the major surface 22' of the pad 21.

If however, as shown in FIG. 10, the hook 24 is not correctly inserted in the heart muscle 26, then the improvement of the present invention becomes necessary and as previously stated, such improvement can be used in all the electrodes, so as to be always on the safe side.

More particularly, when the tip 24' is inserted into the heart muscle 26, a certain resistance may exist against the insertion which would not allow that tip 24' reaches a position to face the major surface 22' of platform 21 of the electrode member 14. As may be seen in FIG. 10, in this event the tangent line 28 forms with the tangent line 27 an obtuse angle (which is not an anchoring angle), so that the ejecting force 29 becomes resolved into two directions parallel or coaxial with said tangent lines 27 ind 28 and the resulting force is in the same general direction, whereby the movement or beating of the heart muscle 26 will eject the hook 24 from the muscle 26. In this case the anchoring means or more particularly the straight shaped needles 25, 25' create the acute anchoring angle, which would have been provided if the tip 24' were in the correct position. In fact the needles 25 define each an axis 30 which forms an acute angle both with tangent line 27 as well as with tangent line 28, thereby assuring a pertinent correct anchoring of the electrode member 14.

It will be evident to those skilled in the art, that the same effect can be achieved even if the generally straight shaped needle-like anchoring means were ahead of the hook 24.

In the embodiment shown, two needle-like members 25, 25' are used which are arranged on one and the other side of the hook 24 and which need not to be parallel, but can be of a diverging type with regard to the major surface 22', bearing in mind that the extremity 18' of the helical conductor 18 enables to insert the hook according to different sloped planes with regard to the major surface 22' and thus, upon the needles 25 and 25' being divergent it is always sure that the desired anchoring is achieved.

As an alternative, a single needle-like anchoring means could be used, which may be located in the same vertical plane (not shown) as the hook 24, when in the position as shown in FIG. 1.

Furthermore, it is not a fundamental requirement that the needle-like anchoring means 25, 25' project from the major surface 22', they could for instance project out of the side portions of the pad 21 or even from the opposite major surface 22 provided that their tips project beyond and above the flat major surface 22' from which the hook 24 project. What is important is that the needle-like anchoring means has a tip portion and an integral general straight portion, which defines the pertinent axis 30 which will cross at an acute angle the tangent line 28, as explained in relationship with FIG. 10.

The resiliency of pad 21 enables the surgeon to grip the hook 24, 124 or 224 with the aid of a suitable tool such as a hook or needle holder, and by applying directed pressure to insert it into the heart muscle 26. The swivelable coil extremity 18' provides the necessary freedom of movement for the hook 24 as the pad 21 resiliently yields during this operation. As soon as the surgeon withdraws the gripping tool, the pad regains its original shape and abuts against the outside surface of the heart, i.e., the epicardium, at which instant the needle-like anchoring means 25, 25' will penetrate likewise the epicardium and if necessary the surgeon can cooperate therewith by exerting a pressure onto the surface 22 of the pad 21, thereby fully anchoring the needles 25, 25' in the flesh.

Obviously the needles 25, 25' as such can be of any suitable structure, they may be actually straight or slightly curved and they may also, if desired be connected to the same source of electrical pulses, for secondary additional stimuli.

It will thus be seen, that no special suturing step is required for attaching the pad to the heart. The resiliency of the pad maintains its contact with the epicardium surface in spite of ongoing heart beat and thus, prevents the hook from detaching itself, thereby insuring continuity of electrical stimulation of the heart by the electrical pulses.

The overall length of the electrode 14 may be up to 140 cm, preferably 105 cm. The height of the tip 24' of the hook 24, 124, or 224 above the pad surface 22' may vary from a few millimeters to about 3 cm. A pad surface of not more 16 cm$^2$, usually 2–5 cm$^2$ has been found highly suitable. The length of the needless 25, 25' is approximately 0.5 to 20 mm.

Needless to say that the extremity 18' could as well project out of the major surface 22' adjacent the stem 16; so that the curved portion 30 of the electric conductor 18 becomes superfluous. The tip 24' of the hook 24 would then be oriented towards a portion of the major surface 22' at the forward end of the pad 21.

I claim:

1. A catheter-type member for an implantable pacemaker, insertable from without through the epicardium into the heart muscle for cardiac stimulation, comprising:

a holder of dielectric material including a stem and an enlarged elastic pad having a substantially flat major surface;

conductor means connectable to an external source of electric pulses, said conductor means extending through said stem into said pad and forming therein a helically coiled portion projecting outwardly from said major surface, said helically coiled portion terminating beyond said major surface in an arcuately curved electricity conducting hook of generally semi-circular shape, rising from the outwardly projecting helically coiled portion and being located above said major surface and having a tip pointing back towards said major surface;

at least one stationary generally straight shaped spaced-apart anchoring needle projecting beyond and diverging from said substantially flat major surface at such an angle that its axis crosses at an acute angle the tangent line passing said generally semi-circular shaped-hook at the point of connection with the outwardly projecting helically coiled portion.

* * * * *